United States Patent [19]

Grabley

[11] Patent Number: 4,638,086
[45] Date of Patent: Jan. 20, 1987

[54] PROCESS FOR THE RACEMIZATION OF OPTICALLY ACTIVE AMINOACIDS

[75] Inventor: Susanne Grabley, Kelkheim, Fed. Rep. of Germany

[73] Assignee: Hoechst Aktiengesellschaft, Frankfurt am Main, Fed. Rep. of Germany

[21] Appl. No.: 654,266

[22] Filed: Sep. 25, 1984

[30] Foreign Application Priority Data

Sep. 27, 1983 [DE] Fed. Rep. of Germany ....... 3334849

[51] Int. Cl.[4] ............................................. C07B 55/00
[52] U.S. Cl. .................................... 562/401; 562/443; 562/444; 562/445; 562/446; 562/450; 562/553; 562/557; 562/559; 562/560
[58] Field of Search .......................................... 562/401

[56] References Cited

U.S. PATENT DOCUMENTS

| 2,071,327 | 2/1937 | Bley | 562/401 |
|---|---|---|---|
| 3,213,106 | 10/1965 | Sasaji et al. | 562/401 |
| 3,458,568 | 7/1969 | Ogasawara et al. | 562/401 |
| 3,796,750 | 3/1974 | Schubel et al. | 562/401 |
| 3,979,457 | 9/1976 | Fujii et al. | 562/401 X |
| 3,991,077 | 11/1976 | Uzuki et al. | 562/401 X |
| 4,226,941 | 10/1980 | Goi et al. | 435/280 |
| 4,260,815 | 4/1981 | Kazan et al. | 562/401 |
| 4,389,488 | 6/1983 | Grabley et al. | 435/280 |
| 4,401,820 | 8/1983 | Chibata et al. | 562/401 X |

FOREIGN PATENT DOCUMENTS 1369462 10/1974 United Kingdom .

Primary Examiner—Natalie Trousof
Assistant Examiner—Vera C. Clarke
Attorney, Agent, or Firm—Finnegan, Henderson, Farabow, Garrett & Dunner

[57] ABSTRACT

The racemization of optically active aminoacids (including their N-acyl derivatives) by heating with carboxylic acids takes place particularly readily with carboxylic acids of low volatility. Only catalytic quantities of acid are needed; it is advantageous to use equimolar quantities or an excess, which serves as a diluent. A reaction mixture from an enzymatic racemate resolution can be heated directly for the purpose of racemization, after separation of the L-aminoacid and the water.

10 Claims, No Drawings

PROCESS FOR THE RACEMIZATION OF OPTICALLY ACTIVE AMINOACIDS

In biologically active compounds, one of the optical antipodes is frequently more active than the other or is the only active one and hence more effective than the racemate. Many processes have therefore already been developed for the resolution of optical antipodes, these processes including the enzymatic resolution of N-acyl-D,L-aminoacids, where an acylase only deacylates the L-component while the N-acyl-D-aminoacid remains unchanged (British Patent Specification No. 1,369,462, German Offenlegungsschriften Nos. 2,446,320 and 2,939,269, and German Patent Specification No. 3,048,612).

Thus, these processes yield a product mixture of free L-aminoacid, the carboxylic acid liberated in the deacylation and the unchanged N-acyl-D-aminoacid. After isolation of the desired L-aminoacid, the unchanged D-acyl compound thus remains as a mixture with the liberated carboxylic acid. It is already known to racemize this N-acyl-D-aminoacid and to recycle the racemate into the process. This has been achieved by melting this compound after separation of the water - if appropriate in the form of an azeotropic mixture (German Offenlegungsschrift No. 2,446,320). Other processes racemize under the action of acetic anhydride and/or acetic acid (German Offenlegungsschriften Nos. 1,963,991 and 2,939,269 and British Patent Specification No. 1,369,462) or with the aid of special solvents including lower fatty acids (German Offenlegungsschrift No. 2,352,579). In the case of this last process, it has also already been pointed out that, if appropriate, it is possible to dispense with the separation of the liberated acid. However, only acetyl compounds were used in the examples, acetic acid thus being liberated - this is a lower fatty acid which is anyway designated as a special solvent.

It has now been found that optically active aminoacids can be racemized in a particularly advantageous manner by heating with carboxylic acids if these carboxylic acids are of low volatility. The term "aminoacids" here includes the free acid, the N-acyl derivatives and the salts. Preferred embodiments of this invention are illustrated in greater detail below:

Only catalytic quantities of carboxylic acid of low volatility need to be used, for example a quantity of 1 to 10 mol %. However, it is also possible to use larger quantities of carboxylic acid, for example equimolar quantities or an excess of acid, in which case the acid can serve as a solvent or diluent. By contrast, the addition of inert solvents or diluents brings no advantage and the reaction is therefore preferably carried out in the absence of such inert solvents or diluents.

It is preferred to employ equimolar quantities of carboxylic acid when a reaction mixture from an enzymatic racemate resolution is used and the carboxylic acid cleaved is of low volatility. In this case, the reaction mixture is thus heated directly for the purpose of racemization, after separation of the desired L-aminoacid and removal of the water.

The racemization is appropriately carried out in a temperature range from 80° to 200°, preferably 130° to 190° and especially 160° to 180° C., higher temperatures corresponding to shorter reaction times. In general, the racemization takes place within 5-30 minutes and without noticeable decomposition of starting material or product.

The separation of the carboxylic acid of low volatility from the racemization product can be carried out on the basis of the different $pK_a$ value, for example with the aid of ion exchangers, but more advantageously on the basis of the different solubility, appropriately by means of extraction with an organic solvent. Non-polar to moderately polar solvents are preferred, for example aliphatic, cycloaliphatic or aromatic hydrocarbons such as hexane, cyclohexane or toluene, halogeno-hydrocarbons such as methylene chloride or chloroform, ethers such as diethyl ether, glycol dimethyl ether or tetrahydrofuran, and esters such as ethyl acetate. A suitable solvent can be tested in each case by means of a simple preliminary experiment.

The component separated off, which is generally the more readily soluble carboxylic acid, can be recovered from the solution by known methods, for example by distillation or crystallization.

Preferred carboxylic acids of low volatility are aromatic compounds, such as benzoic acid, and araliphatic acids, such as phenylacetic acid, and their derivatives monosubstituted or polysubstituted on the nucleus by identical or different substituents from the group comprising halogen, preferably bromine or fluorine, in particular chlorine, lower alkyl, in particular methyl, lower alkoxy, in particular methoxy, hydroxy or acyloxy, in particular acetoxy, or nitro.

Preferred optically active aminoacids which are racemized according to the invention correspond to the formula

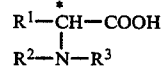

in which $R^1$ denotes optionally substituted lower alkyl or phenyl, $R^2$ denotes hydrogen or together with $R^1$ denotes lower alkylene and $R^3$ denotes hydrogen or acyl, possible acyl groups being especially those for which an acylase is available for racemate resolution. In another preferred embodiment, $R^3$ can be the acyl radical of a carboxylic acid of low volatility, because in this case13 as explained above—the mixture remaining after enzymatic racemate resolution and separation of the liberated aminoacid and the water can be recycled directly into the racemization according to the invention.

Preferred substituents on the lower alkyl group $R^1$ are those radicals which occur in natural aminoacids, that is to say hydroxy mercapto, lower alkylmercapto, carboxy, carboxamido, amino, guanidino, indolyl, imidazolyl, phenyl or substituted phenyl, in particular hydroxyphenyl, it being possible for the hydroxy, mercapto and basic groups to be free or acylated. Another preferred substituent on the group $R^1$ is the lower alkylphosphino group, $R^1$ being in particular the 2-(methylphosphino)ethyl radical.

The invention is illustrated in greater detail in the examples which follow.

EXAMPLE 1

5.4 g of N-phenacetyl-L-methionine are mixed with 2.7 g of phenylacetic acid and the mixture is heated rapidly to 180° C., with stirring. At this temperature, the optical rotation of the reaction mixture drops to 0° within 5 to 10 minutes.

After extraction of the phenylacetic acid with diethyl ether, 5 g (93 % of theory) of N-phenacetyl-D,L-methionine are isolated.

EXAMPLE 2

5.7 g of N-phenacetyl-D-phenylalanine are heated with 2.7 g of phenylacetic acid to 170° C. in a manner corresponding to Example 1. About 90% has racemized after 10 minutes and the racemization is complete after 20 minutes.

After separation of the phenylacetic acid by extraction with methylene chloride, 5.1 g (90% of theory) of N-phenacetyl-D,L-phenylalanine can be isolated.

EXAMPLE 3

3 g of N-phenacetyl-D-phenylglycine are mixed with 1 g of phenylacetic acid and the mixture is heated to 170° C. The racemization has ended after 15 minutes.

EXAMPLE 4

4.7 g of N-phenacetyl-L-valine are heated with 1.5 g of phenylacetic acid to 180° C. After 5 minutes, the optical rotation has dropped to 0°.

After extraction with cyclohexane, 4 g of N-phenacetyl-D,L-valine (85% of theory) can be obtained.

EXAMPLE 5

3 g of N-benzoyl-L-methionine are mixed with 1.6 g of phenylacetic acid and the mixture is heated to 165° C. The racemization is complete after 15 minutes. After extraction with methylene chloride/cyclohexane, 2.6 g (78% of theory) of N-benzoyl-D,L-methionine remain.

EXAMPLE 6

5.1 g of N-benzoyl-L-methionine are treated with 2.5 g of benzoic acid and the mixture is heated in an oil bath at 180° C., with stirring. The racemization has ended after 25 minutes.

After removal of the benzoic acid, 4.1 g (82% of theory) of N-benzoyl-D,L-methionine are obtained.

EXAMPLE 7

A mixture of 15 g of D-2-phenacetylamino-4-methylphosphinobutyric acid and 6.8 g of phenylacetic acid is heated rapidly to 180° C. and the racemization is followed by taking samples and measuring the optical rotation. After 20–25 minutes, the optical rotation has dropped to 0°. After extraction with toluene/water, 13.8 g (92% of theory) of D,L-2-phenacetylamino-4-methylphosphinobutyric acid remain.

EXAMPLE 8

5 g of D-2-amino-4-methylphosphinobutyric acid are mixed with 3.7 g of phenylacetic acid and the mixture is heated to 180° C. within 30 minutes. At this temperature, the racemization is complete after 5 minutes. After extraction with methylene chloride 4.5 g (90 %) of D,L-2-amino-4-methyl-phosphinobutyric acid are isolated.

EXAMPLE 9

A mixture of 5 g of ammonium L-2-amino-4-methylphosphinobutyrate and 3.4 g of phenylacetic acid is heated to 180° C. After 30 minutes, the optical rotation has dropped to 0°. After extraction with chloroform, 4.6 g (92 % of theory) of ammonium D,L-2-amino-4-methylphosphinobutyrate are obtained.

In place of the ammonium salt, it is also possible to use an alkali metal salt, for example the sodium salt.

In this specification there are cited some German Offenlegungsschriften (DE-OS) and published European Patent Applications (EP-A) which correspond to the following U.S. patents (U.S. Pat. Nos.—which hereby are incorporated by reference):

| DE-OS | 1 963 991 | US-PS | 3 796 750 |
|---|---|---|---|
|  | 2 352 579 |  | 3 991 077 |
|  | 2 446 320 |  | 3 979 457 |
|  | 2 732 301 |  | 4 247 643 |
|  | 2 939 269 |  | 4 226 941 |
|  | 3 048 612 |  | 4 389 488 |
| EP-A | 43 169 |  | 4 397 949 |
|  | 52 365 |  | 4 412 000 |

What is claimed is:

1. A process for racemization of optically active amino acids which comprises heating said amino acids with an effective amount of benzoic or phenylacetic acid or their derivatives which are monosubstituted or polysubstituted on the nucleus by identical or different substituents selected from the group consisting of halogen, lower alkyl, lower alkoxy, hydroxy, acyloxy, and nitro.

2. The process as claimed in claim 1, wherein equimolar quantities of said benzoic or phenylacetic acid are used.

3. The process as claimed in claim 1, wherein an excess of said benzoic or phenylacetic acid is used.

4. The process as claimed in claim 2, wherein a reaction mixture from an enzymatic racemate resolution, from which the L-aminoacid and the water have been removed, is racemized.

5. The process as claimed in claim 1, wherein the racemization is carried out at 80° to 200° C.

6. The process as claimed in claim 5, wherein the racemization is carried out at 130° to 190° C.

7. The process as claimed in claim 6, wherein the racemization is carried out at 160°–180° C.

8. A process for racemization of optically active amino acids of formula I

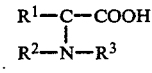

wherein $R^1$ is a lower alkyl which can be optionally substituted or phenyl, $R^2$ is hydrogen or $R^2$, taken together with $R^1$, is a lower alkylene, and $R^3$ is hydrogen or acyl, wherein said racemization occurs by heating said optically active amino acids of formula I to 80°–200° C. with an effective amount of benzoic or phenylacetic acid or their derivatives which are monosubstituted or polysubstituted on the nucleus by identical or different substituents selected from the group consisting of halogen, lower alkyl, lower alkoxy, hydroxy, acyloxy, and nitro.

9. The process as claimed in claim 8, wherein the lower alkyl group $R^1$ of the amino acid of formula I is one which occurs in natural amino acids.

10. The process as claimed in claim 8, wherein the lower alkyl group $R^1$ of the amino acid of formula I is a lower alkylphosphino group.

* * * * *